United States Patent
Lee et al.

(10) Patent No.: US 11,160,726 B2
(45) Date of Patent: Nov. 2, 2021

(54) PLASMA STIMULATION APPARATUS AND ACUPUNCTURE TREATMENT APPARATUS INCLUDING THE SAME

(71) Applicant: FEAGLE CO., LTD, Yangsan-si (KR)

(72) Inventors: Hyunyoung Lee, Busan (KR); Jeonghae Choi, Busan (KR); Youngmin Kim, Gimhae-si (KR)

(73) Assignee: FEAGLE CO., LTD, Yangsan-si (KR)

( * ) Notice: Subject to any disclaimer, the term of this patent is extended or adjusted under 35 U.S.C. 154(b) by 185 days.

(21) Appl. No.: 16/322,098

(22) PCT Filed: Aug. 2, 2016

(86) PCT No.: PCT/KR2016/008482
§ 371 (c)(1),
(2) Date: Jan. 30, 2019

(87) PCT Pub. No.: WO2018/026027
PCT Pub. Date: Feb. 8, 2018

(65) Prior Publication Data
US 2019/0183728 A1   Jun. 20, 2019

(51) Int. Cl.
| | |
|---|---|
| *A61N 1/44* | (2006.01) |
| *A61H 39/08* | (2006.01) |
| *A61N 1/08* | (2006.01) |
| *A61N 1/05* | (2006.01) |
| *A61N 1/30* | (2006.01) |
| *A61N 1/32* | (2006.01) |
| *A61N 1/36* | (2006.01) |

(52) U.S. Cl.
CPC .............. *A61H 39/08* (2013.01); *A61N 1/08* (2013.01); *A61N 1/44* (2013.01); *A61N 1/0502* (2013.01); *A61N 1/30* (2013.01); *A61N 1/325* (2013.01); *A61N 1/36021* (2013.01)

(58) Field of Classification Search
CPC . A61H 39/08; A61N 1/08; A61N 1/44; A61N 1/0502
See application file for complete search history.

(56) References Cited

U.S. PATENT DOCUMENTS

| | | | |
|---|---|---|---|
| 2016/0001052 | A1 | 1/2016 | Zucker |
| 2016/0023183 | A1 | 1/2016 | Levin |
| 2018/0325728 | A1* | 11/2018 | Weikart ............... A61F 9/0017 |

FOREIGN PATENT DOCUMENTS

| | | |
|---|---|---|
| JP | 07-003643 U | 1/1995 |
| JP | 2014-165147 A | 9/2014 |
| KR | 10-2012-0034356 A | 4/2012 |
| KR | 10-1147397 B1 | 5/2012 |
| KR | 10-2015-0071181 A | 6/2015 |
| KR | 10-2016-0015894 A | 2/2016 |
| KR | 10-2016-0058934 A | 5/2016 |
| KR | 10-1633586 B1 | 6/2016 |

OTHER PUBLICATIONS

International Search Report in International Application No. PCT/KR2016/008482, dated May 22, 2017.

* cited by examiner

*Primary Examiner* — Joseph M Dietrich
(74) *Attorney, Agent, or Firm* — Park, Kim & Suh, LLC

(57) ABSTRACT

The inventive concept relates to a plasma stimulation apparatus and an acupuncture treatment apparatus including the same. The plasma stimulation apparatus includes a cover that covers a stimulation medium inserted into a body part and a plasma generation unit that generates plasma and supplies the plasma to the cover.

12 Claims, 19 Drawing Sheets

PLASMA STIMULATION APPARATUS AND ACUPUNCTURE TREATMENT APPARATUS INCLUDING THE SAME

CROSS-REFERENCE TO RELATED APPLICATIONS

This application is the National Stage filing under 35 U.S.C. 371 of International Application No. PCT/KR2016/008482, filed on Aug. 2, 2016, the contents of which are all hereby incorporated by reference herein in their entirety.

TECHNICAL FIELD

Embodiments of the inventive concepts described herein relate to a plasma stimulation apparatus and an acupuncture treatment apparatus including the same.

BACKGROUND

Acupuncture is a form of medicine in which a thin and exquisite needle is inserted into a specific part of a body to stimulate the body part, thereby treating a disease. After inserting a needle into a body, an oriental medical doctor turns the inserted needle, or pushes the needle deeper into the skin and pulls out the needle, to increase physical stimulation.

Furthermore, there is electrical acupuncture in which a needle is inserted into a body and an electrical signal is applied to the needle. In the electrical acupuncture, two or more needles are inserted into a body part, and a positive electrode terminal and a negative electrode terminal of a power supply are connected to the needles to apply acupuncture stimulation and electrical stimulation to the body part into which the needles are inserted.

However, strictly speaking, the electrical acupuncture applies stimulation by allowing electric current to flow through a tissue between meridian points into which two needles are inserted, rather than stimulating the meridian points into which the needles are inserted. Therefore, the electrical acupuncture does not intensively stimulate the meridian points.

SUMMARY

Technical Problem

Embodiments of the inventive concepts provide a plasma stimulation apparatus and an acupuncture treatment apparatus for applying physical stimulation, electrical stimulation, and chemical stimulation to a body part into which a stimulation medium such as a needle for applying stimulation to a body is inserted, through the stimulation medium, thereby effectively stimulating a meridian point.

Embodiments of the inventive concepts provide a plasma stimulation apparatus and an acupuncture treatment apparatus for preventing over-current from flowing through a stimulation medium during stimulation treatment using plasma.

Embodiments of the inventive concepts provide a plasma stimulation apparatus and an acupuncture treatment apparatus for adjusting the distribution of electrons and positive ions in a cover that covers a stimulation medium, thereby improving effects of stimulation treatment using plasma.

Embodiments of the inventive concepts provide a plasma stimulation apparatus and an acupuncture treatment apparatus for providing plasma mixed with a medicine to a body part, thereby improving effects of stimulation treatment.

Technical Solution

According to an exemplary embodiment, a plasma stimulation apparatus includes a cover that covers a stimulation medium inserted into a body part and a plasma generation unit that generates plasma and supplies the plasma to the cover.

The cover may be made of a dielectric material.

The cover may include a supply hole through which the cover receives the plasma from the plasma generation unit.

The plasma stimulation apparatus may further include a plasma passage part that is located between the plasma generation unit and the supply hole and that passes the plasma, with the plasma passage part in a grounded state.

The plasma passage part may include a mesh that blocks an area through which the plasma passes.

The cover may include an exhaust hole for discharging an exhaust gas, the exhaust hole being located adjacent to a contact surface of the cover that makes contact with the body part.

The plasma generation unit may include a dielectric material having an empty space through which a source gas for generating the plasma passes, a first electrode located inside the dielectric material, and a second electrode that surrounds at least part of the dielectric material.

The plasma generation unit may receive an inert gas as the source gas.

The cover may further include a plasma distribution adjustment unit that adjusts distribution of the plasma in the cover.

The plasma distribution adjustment unit may include at least one adjustment electrode included in the cover and an adjustment power supply that applies an electrical signal to the adjustment electrode.

The adjustment electrode may include at least one of a first adjustment electrode formed on a sidewall of the cover that surrounds the stimulation medium and a second adjustment electrode formed on an upper wall of the cover that faces the body part.

The adjustment power supply may apply a direct current signal to the adjustment electrode.

The adjustment power supply may apply a direct current signal with a negative polarity to the first adjustment electrode and a direct current signal with a positive polarity to the second adjustment electrode.

The plasma stimulation apparatus may further include a medicine applied to at least one of the plasma passage part and an inner surface of the cover.

According to an exemplary embodiment, an acupuncture treatment apparatus includes at least one needle inserted into a body part, a cover that covers the needle inserted into the body part, and a plasma generation unit that generates plasma and supplies the plasma to the cover.

Advantageous Effects

According to the embodiments of the inventive concept, physical stimulation, electrical stimulation, and chemical stimulation may be applied to the body part into which the stimulation medium is inserted, through the stimulation medium, thereby effectively stimulating a meridian point.

According to the embodiments of the inventive concept, over-current may be prevented from flowing through the stimulation medium during stimulation treatment using plasma.

According to the embodiments of the inventive concept, the distribution of electrons and positive ions in the cover that covers the stimulation medium may be adjusted, thereby improving effects of stimulation treatment using plasma.

According to the embodiments of the inventive concept, plasma mixed with the medicine may be provided to the body part during stimulation treatment, thereby improving effects of the stimulation treatment.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Other advantages and features of the inventive concept, and implementation methods thereof will be clarified through the following embodiments to be described in detail with reference to the accompanying drawings. The inventive concept may, however, be embodied in different forms and should not be construed as being limited to the embodiments set forth herein. Rather, these embodiments are provided so that this disclosure is thorough and complete and fully conveys the scope of the inventive concept to a person skilled in the art to which the inventive concept pertains. Further, the inventive concept is only defined by the appended claims.

Even though not defined, all terms used herein (including technical or scientific terms) have the same meanings as those generally accepted by general technologies in the related art to which the inventive concept pertains. The terms defined in general dictionaries may be construed as having the same meanings as those used in the related art and/or a text of the present application and even when some terms are not clearly defined, they should not be construed as being conceptual or excessively formal.

Terms used herein are only for description of embodiments and are not intended to limit the inventive concept. As used herein, the singular forms are intended to include the plural forms as well, unless context clearly indicates otherwise. It will be further understood that the terms "comprise" and/or "comprising" used herein specify the presence of stated features or components, but do not preclude the presence or addition of one or more other features or components. In the specification, the term "and/or" indicates each of listed components or various combinations thereof.

Hereinafter, embodiments of the inventive concept will be described in detail with reference to the accompanying drawings.

Figure 1:
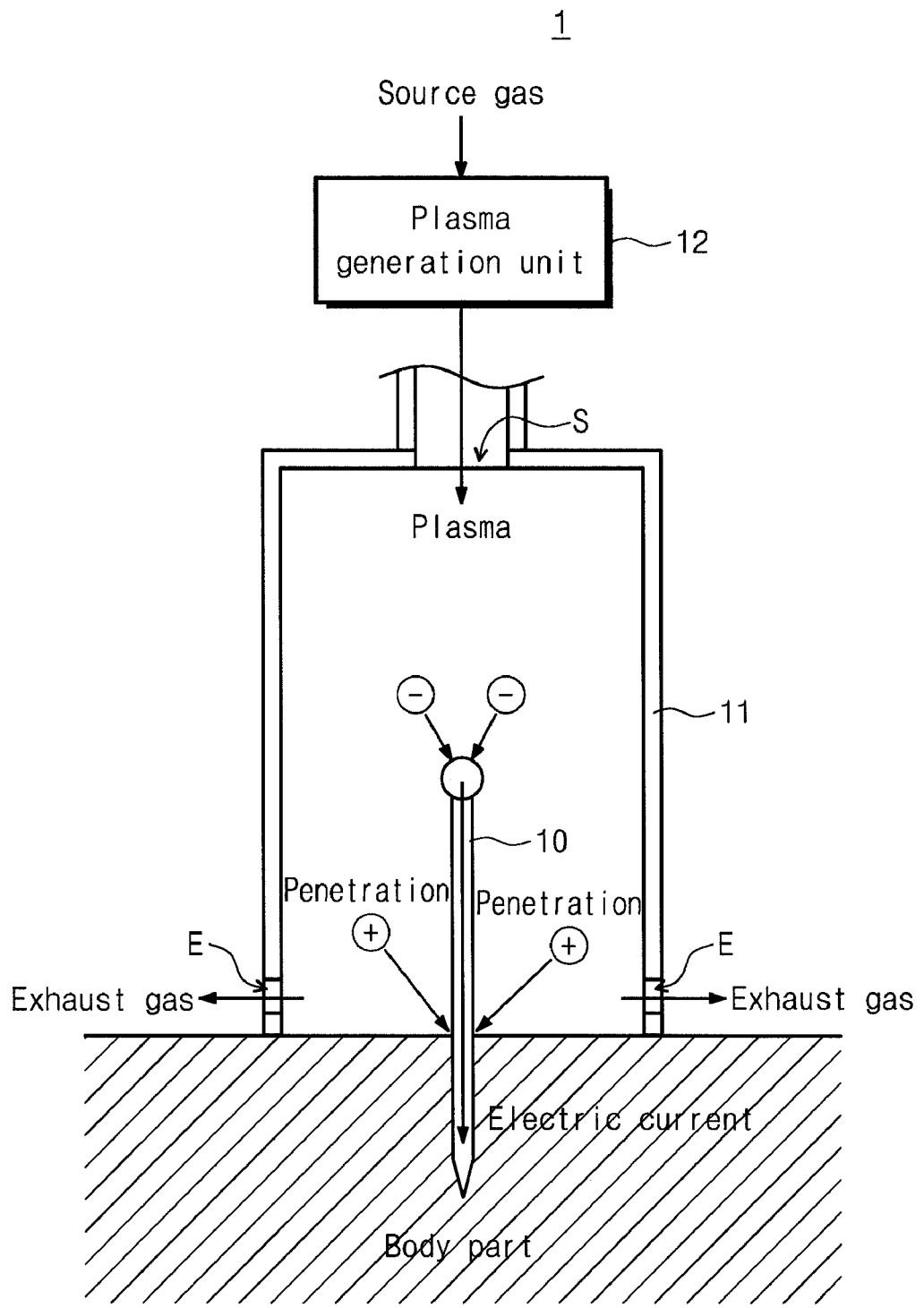
FIG. 1 is a view illustrating a plasma stimulation apparatus according to an embodiment of the inventive concept.

FIG. 1 is a view illustrating a plasma stimulation apparatus 1 according to an embodiment of the inventive concept.

Referring to FIG. 1, the plasma stimulation apparatus 1 includes a cover 11 and a plasma generation unit 12. The cover 11 covers a stimulation medium 10 inserted into a body part. The plasma generation unit 12 generates plasma and supplies the plasma to the cover 11.

According to an embodiment of the inventive concept, the stimulation medium 10 includes a needle. However, the stimulation medium 10 is not limited to needles used for acupuncture in oriental medicine and includes any means inserted into a body and used for stimulation treatment using plasma as in the embodiment of the inventive concept.

The stimulation medium 10 may be made of a conductor. For example, the stimulation medium 10 may be made of, but is not limited to, metal such as iron.

The cover 11 may be made of a dielectric material. Since the cover 11 receives the plasma from the plasma generation unit 12, provides the plasma to the stimulation medium 10 and the body part into which the stimulation medium 10 is inserted, and makes contact with the body part while covering the stimulation medium 10, as will be described below, the cover 11 may be made of a dielectric material to prevent electric current from flowing through the cover 11.

The cover 11 includes a supply hole S through which the cover 11 receives the plasma from the plasma generation unit 12. While the supply hole S in FIG. 1 is formed in the upper surface of the cover 11, the position of the supply hole S is not limited thereto.

Furthermore, the cover 11 may include an exhaust hole E for discharging an exhaust gas. The exhaust hole E may be located adjacent to a contact surface of the cover 11 that makes contact with the body part. For example, as illustrated in FIG. 1, one or more exhaust holes E may be formed in the cover 11 near the body part.

Figure 2:
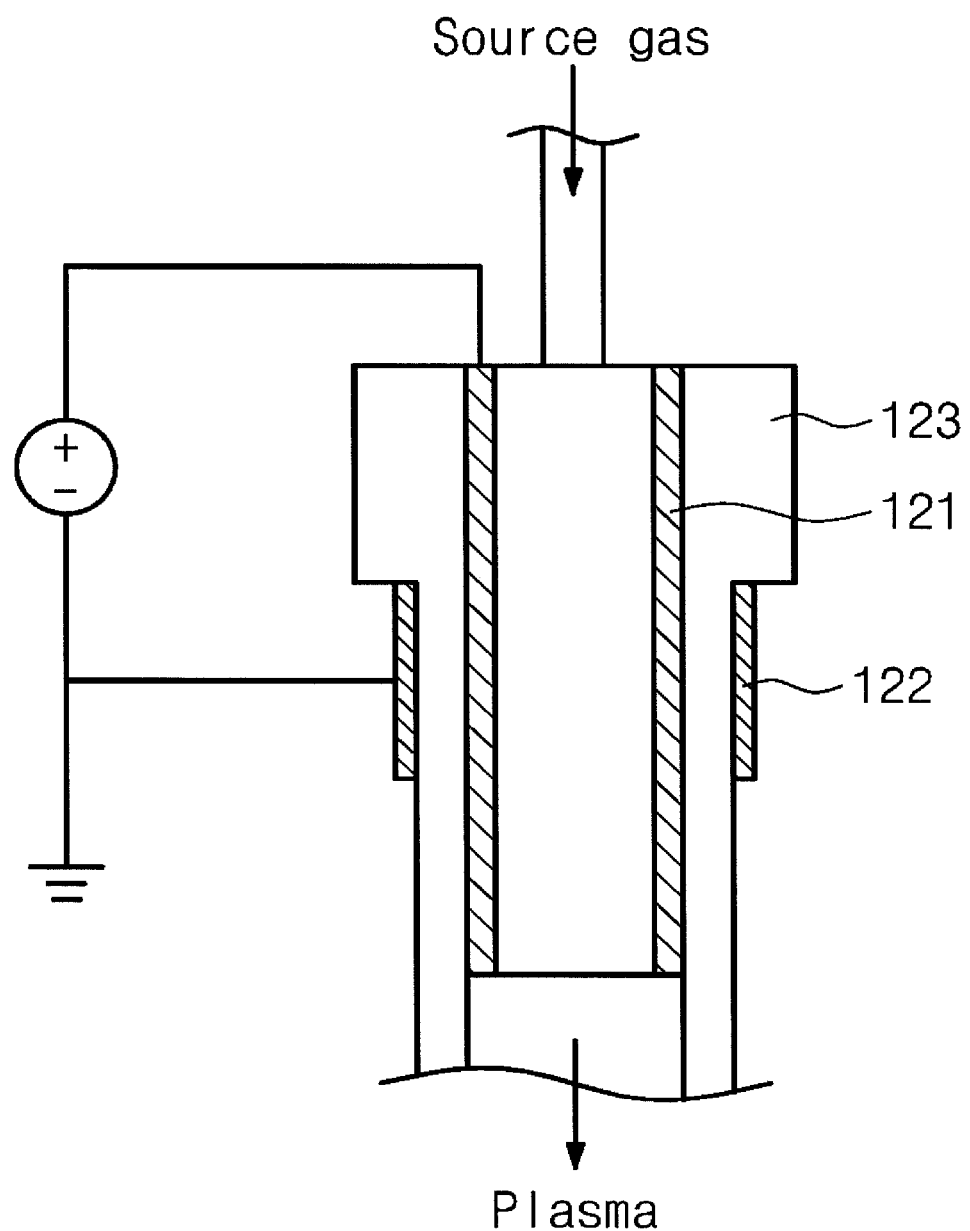
FIG. 2 is a sectional view illustrating a plasma generation unit according to an embodiment of the inventive concept.

FIG. 2 is a sectional view illustrating the plasma generation unit 12 according to an embodiment of the inventive concept.

According to an embodiment of the inventive concept, the plasma generation unit 12 may include a dielectric material 123 having an empty space through which a source gas for generating plasma passes, a first electrode 121 located inside the dielectric material 123, and a second electrode 122 surrounding at least part of the dielectric material 123.

For example, as illustrated in FIG. 2, the first and second electrodes 121 and 122 may face each other with the dielectric material 123 therebetween. Here, the second electrode 122 on the outside of the dielectric material 123 may be disposed to surround a partial area of the first electrode 121 inside the dielectric material 123.

That is, the first electrode 121 and the second electrode 122 may have hollow cylindrical shapes with different diameters and lengths and may be disposed to overlap each other with the dielectric material 123 therebetween. However, the area of the first electrode 121 that overlaps the second electrode 122 corresponds to a partial area of the first electrode 121.

Furthermore, the plasma stimulation apparatus 1 further includes a power supply that supplies power for generating plasma to the plasma generation unit 12.

Referring to FIG. 2, the power supply may apply a power signal to the first electrode 121 and may ground the second electrode 122. The power supply may apply a high-voltage direct current signal or a high-frequency signal as the power signal.

The plasma generation unit 12 receives the source gas. According to an embodiment of the inventive concept, the plasma generation unit 12 may receive an inert gas as the source gas. For example, the plasma generation unit 12 may receive at least one of argon and helium. However, the source gas is not limited thereto, and air or a different type of gas may be used as the source gas.

As described above, in the embodiment of the inventive concept, the stimulation medium 10 inserted into the body part such as a meridian point is covered with the cover 11, and plasma is supplied into the cover 11. Among electrons and positive ions constituting the plasma, the electrons may be transferred to the body part as electric current through the stimulation medium 10 to electrically stimulate the body part, and the positive ions may chemically act on the body part around the stimulation medium 10 to chemically stimulate the body part.

That is, according to the embodiment of the inventive concept, the plasma stimulation apparatus 1 may provide physical stimulation (stimulation by the needle), electrical stimulation (stimulation by the electrons), and chemical stimulation (stimulation by the positive ions) to the body part by using the stimulation medium 10 and the plasma, thereby effectively stimulating the meridian point.

Figure 3:
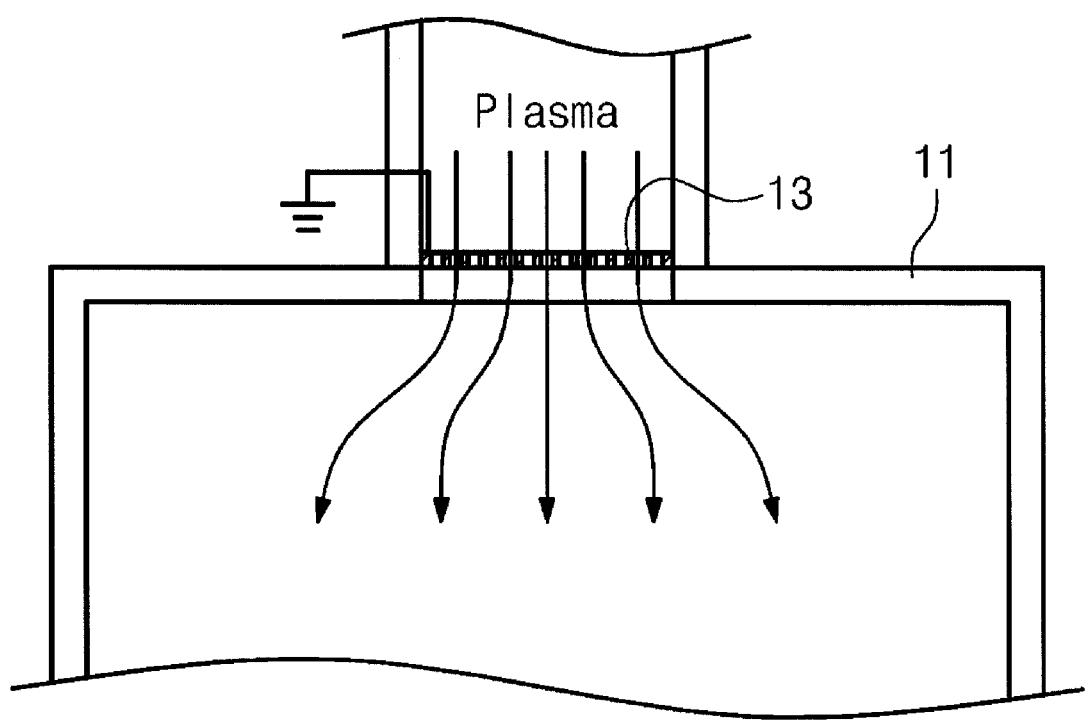
FIG. 3 is a partial sectional view illustrating the plasma stimulation apparatus including a plasma passage part according to an embodiment of the inventive concept.
Figure 4:
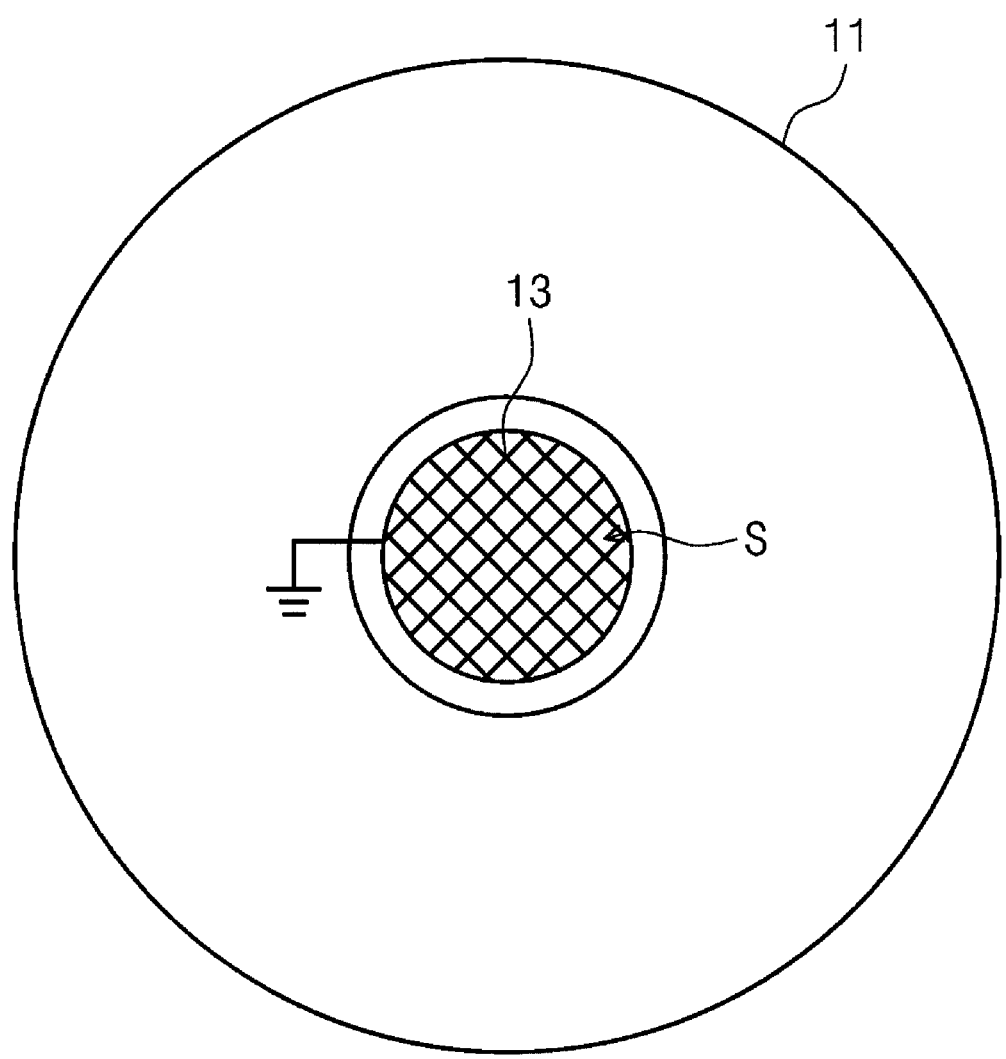
FIG. 4 is a plan view illustrating a cover including the plasma passage part according to an embodiment of the inventive concept.

FIG. 3 is a partial sectional view illustrating the plasma stimulation apparatus 1 including a plasma passage part 13 according to an embodiment of the inventive concept, and FIG. 4 is a plan view illustrating the cover 11 including the plasma passage part 13 according to an embodiment of the inventive concept.

According to an embodiment of the inventive concept, the plasma stimulation apparatus 1 may further include the plasma passage part 13 that is located between the plasma generation unit 12 and the supply hole S and that passes plasma, with the plasma passage part 13 in a grounded state.

For example, as illustrated in FIG. 3, the plasma passage part 13 may be disposed in the supply hole S to pass plasma. However, the position of the plasma passage part 13 is not limited thereto, and the plasma passage part 13 may be disposed at any position between the place where plasma is discharged from the plasma generation unit 12 and the place where the plasma is introduced into the cover 11.

According to this embodiment, the plasma passage part 13 may include a mesh that blocks an area through which plasma passes. For example, as illustrated in FIG. 4, the plasma passage part 13 may be formed in a mesh form and may be disposed to block the area through which the plasma passes. Accordingly, plasma generated by the plasma generation unit 12 and supplied into the cover 11 passes through the plasma passage part 13.

Furthermore, as illustrated in FIGS. 3 and 4, the plasma passage part 13 is grounded. Since the plasma passage part 13 is grounded, electric potential is maintained at 0, and a discharge path from the plasma generation unit 12, through which a high-voltage signal flows, to the stimulation medium 10 may be prevented from being formed in the plasma stimulation apparatus 1. As a result, according to this embodiment, over-current may be prevented from flowing through the stimulation medium 10 due to the plasma supplied into the cover 11.

The cover 11 may further include a plasma distribution adjustment unit that adjusts the distribution of plasma in the cover 11. According to an embodiment of the inventive concept, the plasma distribution adjustment unit may include at least one adjustment electrode included in the cover 11 and an adjustment power supply that applies an electrical signal to the adjustment electrode.

Figure 5:
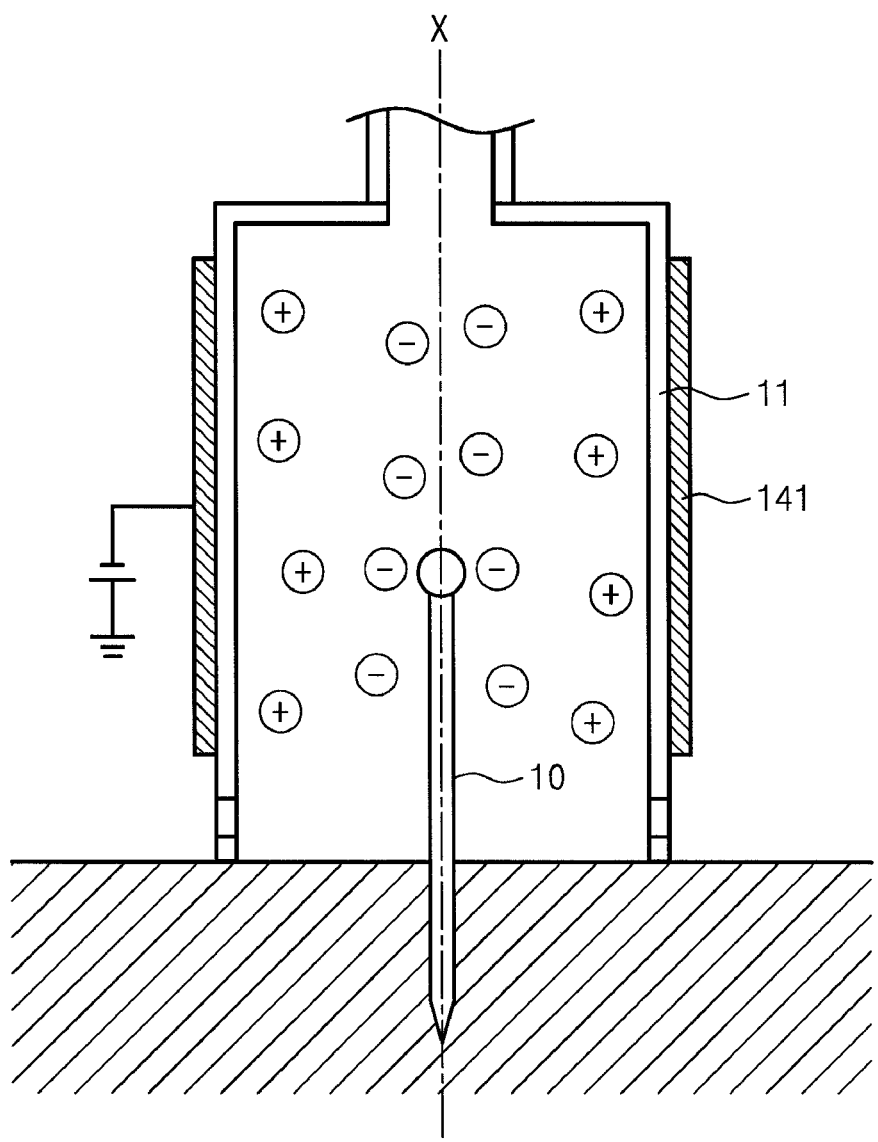
FIGS. 5 and 6 are a sectional view and a plan view illustrating the cover including a plasma distribution adjustment unit according to an embodiment of the inventive concept.
Figure 6:
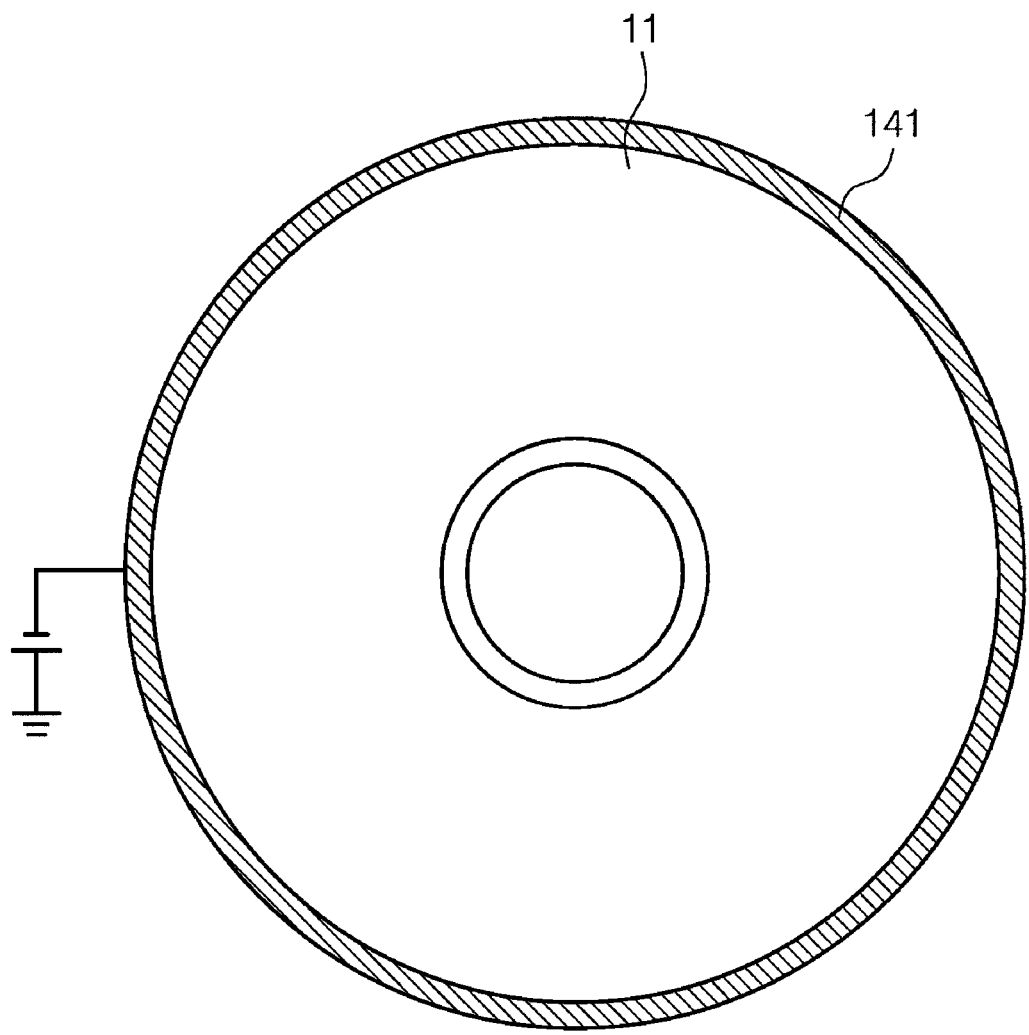

FIGS. 5 and 6 are a sectional view and a plan view illustrating the cover 11 including the plasma distribution adjustment unit according to an embodiment of the inventive concept.

According to an embodiment of the inventive concept, the adjustment electrode may include a first adjustment electrode 141 formed on a sidewall of the cover 11 that surrounds the stimulation medium 10.

For example, as illustrated in FIGS. 5 and 6, the first adjustment electrode 141 may be formed to surround the outer surface of the cover 11 through an angle of 360 degrees about the central axis X of the cover 11.

The adjustment power supply may apply a direct current signal to the first adjustment electrode 141. For example, as illustrated in FIGS. 5 and 6, a direct current signal with a negative polarity may be applied to the first adjustment electrode 141.

In this case, the first adjustment electrode 141 exerts a repulsive force and an attractive force on electrons and positive ions constituting plasma since the direct current signal with a negative polarity is applied to the first adjustment electrode 141. As a result, as illustrated in FIG. 5, the electrons of the plasma supplied into the cover 11 may be located in the central area of the cover 11, and the positive ions may be located in the edge area of the cover 11.

Due to this, the electrons of the plasma may be intensively distributed on the stimulation medium 10 located in the central area of the cover 11, and the positive ions of the plasma may be distributed on the body part around the stimulation medium 10. Accordingly, the plasma stimulation apparatus 1 may effectively provide electrical stimulation through the stimulation medium 10 and chemical stimulation for the body part into which the stimulation medium 10 is inserted.

Figure 7:
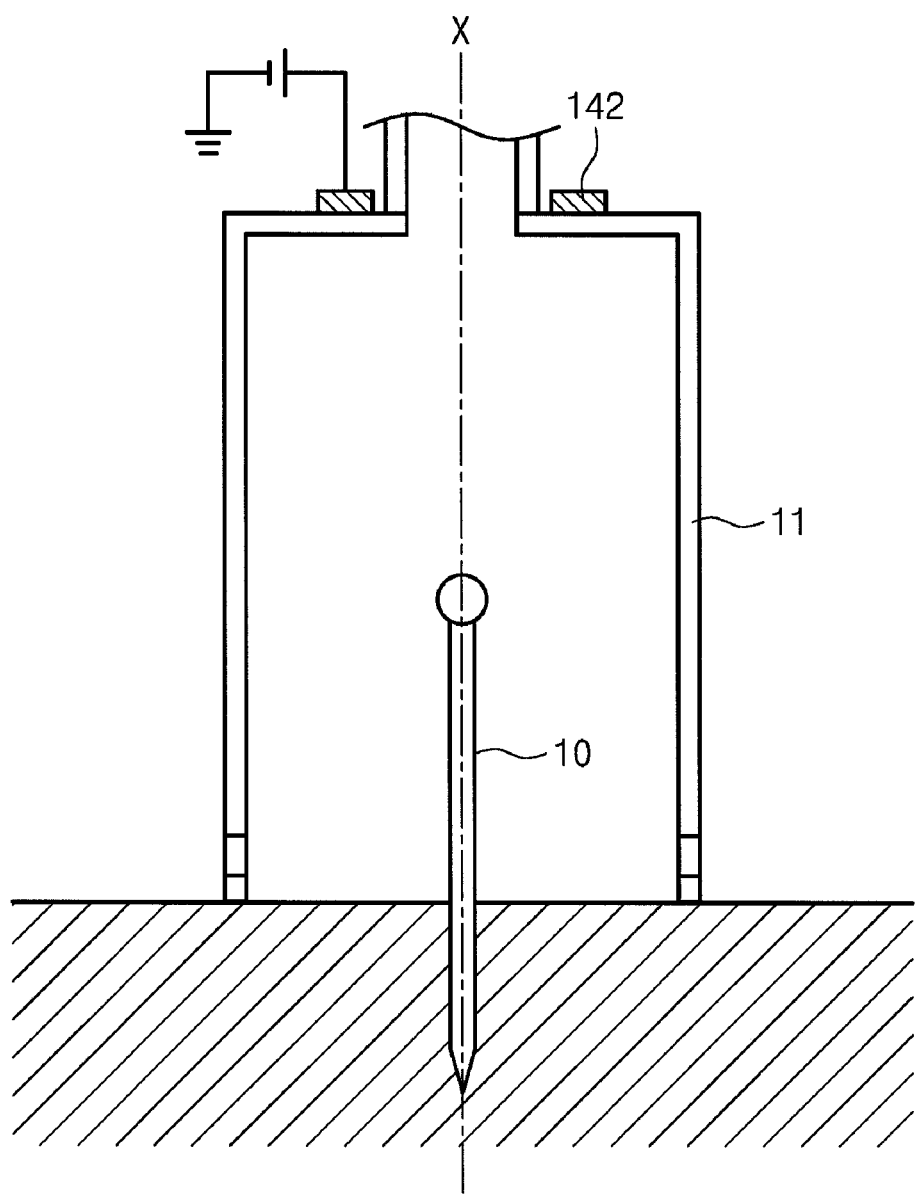
FIGS. 7 and 8 are a sectional view and a plan view illustrating the cover including a plasma distribution adjustment unit according to another embodiment of the inventive concept.
Figure 8:
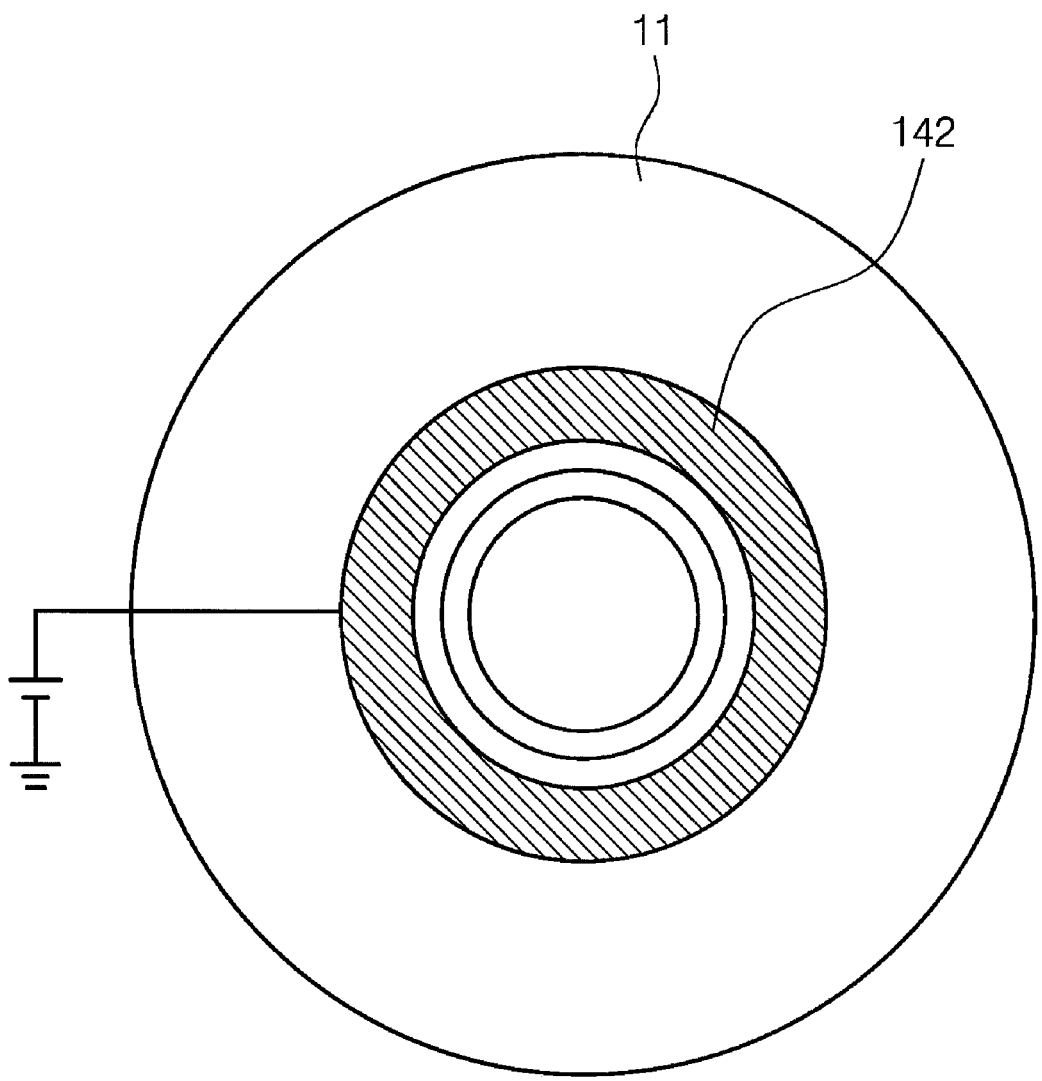

FIGS. 7 and 8 are a sectional view and a plan view illustrating the cover 11 including a plasma distribution adjustment unit according to another embodiment of the inventive concept.

According to another embodiment of the inventive concept, the adjustment electrode may include a second adjustment electrode 142 formed on an upper wall of the cover 11 that faces the body part.

For example, as illustrated in FIGS. 7 and 8, the second adjustment electrode 142 may be formed on an upper surface of the cover 11 through an angle of 360 degrees about the central axis X of the cover 11.

The adjustment power supply may apply a direct current signal to the second adjustment electrode 142. For example, as illustrated in FIGS. 7 and 8, a direct current signal with a positive polarity may be applied to the second adjustment electrode 142.

In this case, the second adjustment electrode 142 exerts an attractive force and a repulsive force on electrons and positive ions constituting plasma since the direct current signal with a positive polarity is applied to the second adjustment electrode 142.

Due to this, the electrons of the plasma may be distributed in an area of the cover 11 (the upper central area in FIGS. 7 and 8) that is close to the second adjustment electrode 142, and the positive ions of the plasma may be distributed in an area of the cover 11 (the edge area and the lower central area in FIGS. 7 and 8) that is far away from the second adjustment electrode 142. Accordingly, the plasma stimulation apparatus 1 may effectively provide electrical stimulation through the stimulation medium 10 and chemical stimulation for the body part into which the stimulation medium 10 is inserted.

Figure 9:
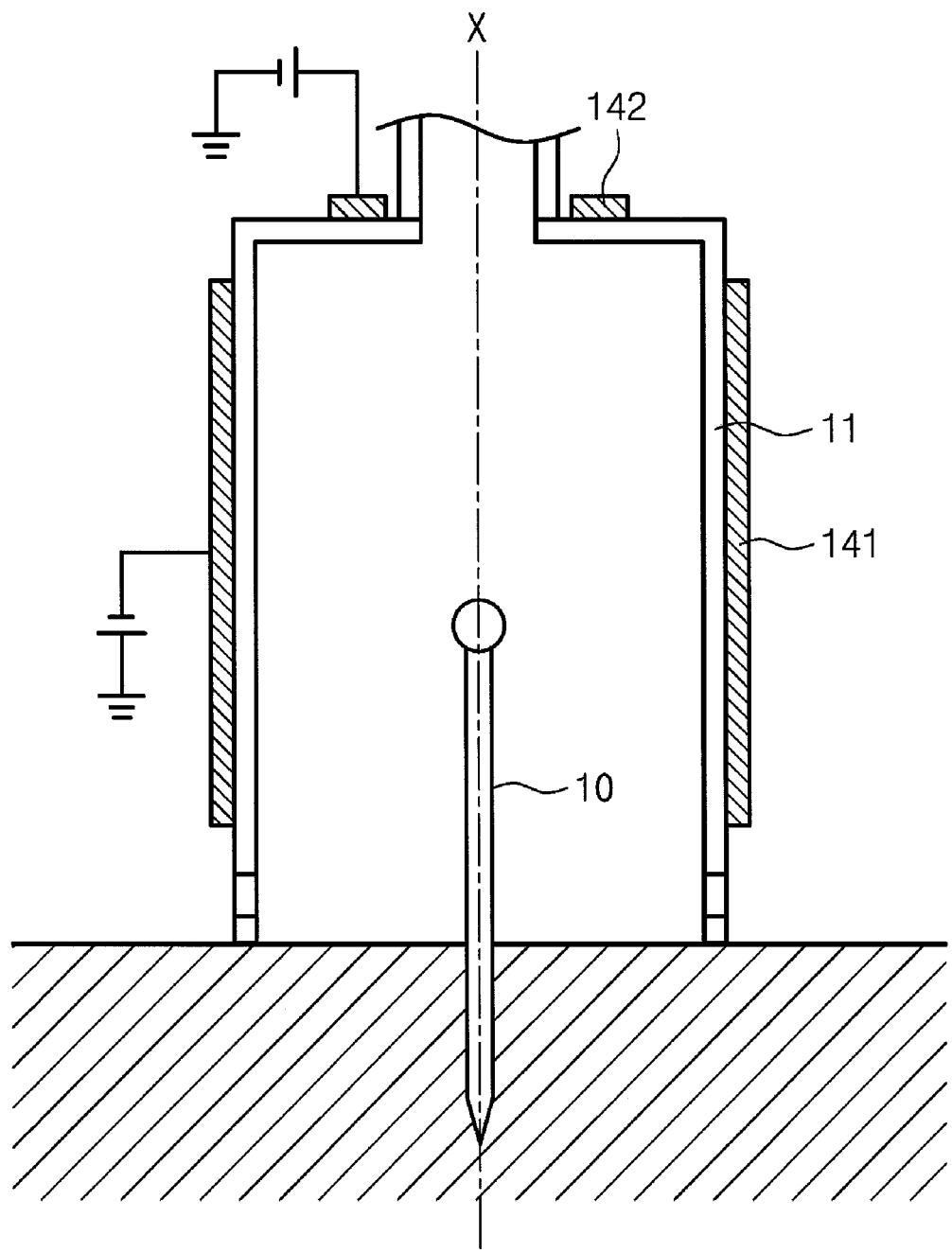
FIGS. 9 and 10 are a sectional view and a plan view illustrating the cover including a plasma distribution adjustment unit according to yet another embodiment of the inventive concept.
Figure 10:
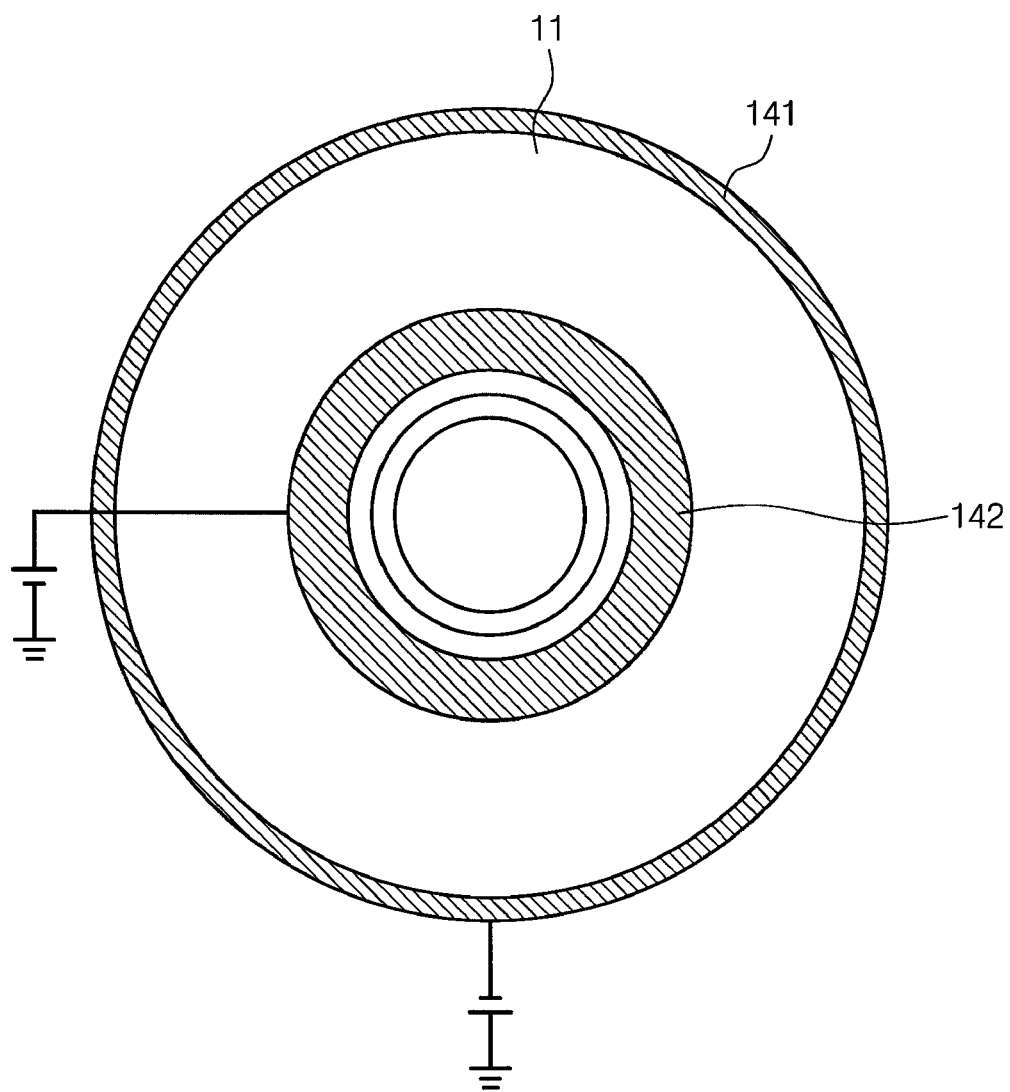

FIGS. 9 and 10 are a sectional view and a plan view illustrating the cover 11 including a plasma distribution adjustment unit according to yet another embodiment of the inventive concept.

According to yet another embodiment of the inventive concept, an adjustment electrode installed on the cover 11 may include both the first adjustment electrode 141 and the second adjustment electrode 142.

The adjustment power supply may apply direct current signals to the first and second adjustment electrodes 141 and 142. For example, as illustrated in FIGS. 9 and 10, a direct current signal with a negative polarity may be applied to the first adjustment electrode 141, and a direct current signal with a positive polarity may be applied to the second adjustment electrode 142.

As described above, the plasma stimulation apparatus 1 may appropriately include the adjustment electrodes on the sidewall and the upper wall of the cover 11 and may apply the direct current signals with positive and negative polarities to the adjustment electrodes. Accordingly, the plasma stimulation apparatus 1 may adjust spatial distribution of electrons and positive ions of plasma in the cover 11, thereby maximizing electrical stimulation through the stimulation medium 10 and chemical stimulation for the body part.

While the adjustment power supply in this embodiment applies the direct current signals to the adjustment electrodes, the adjustment power supply may apply electrical signals with various waveforms to the adjustment electrodes.

Figure 11:
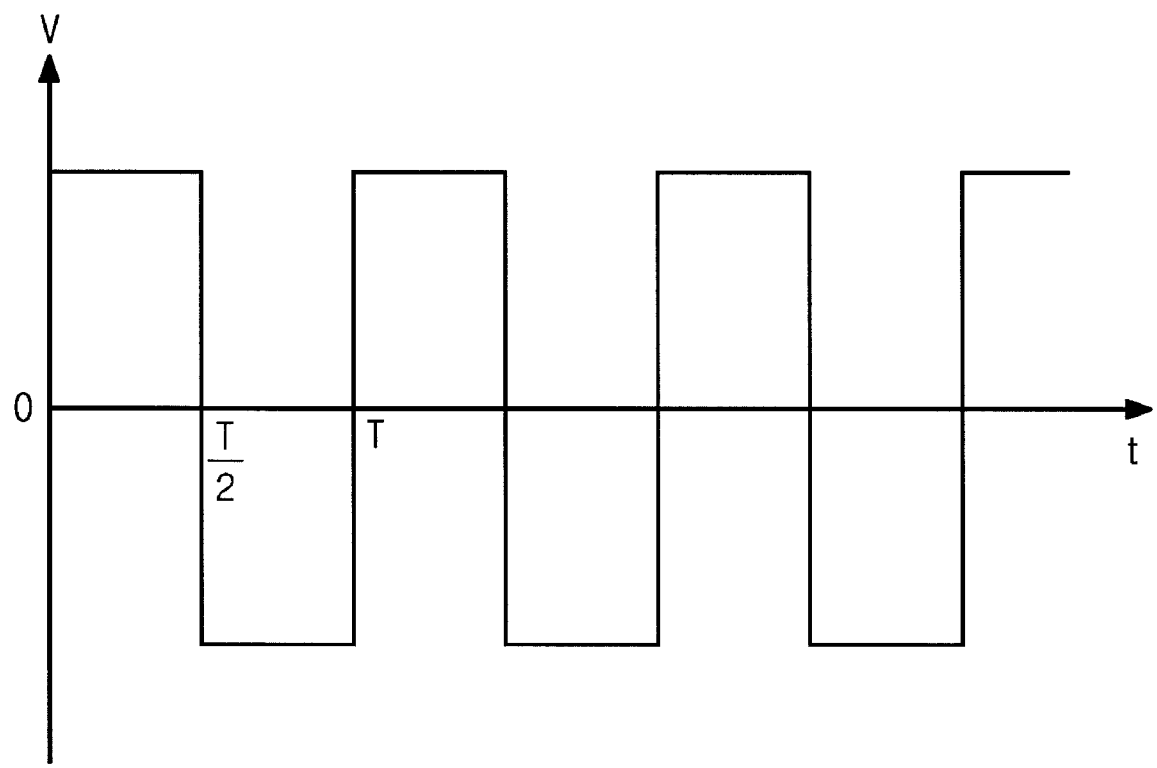
FIGS. 11 to 13 are views illustrating waveforms of electrical signals that an adjustment power supply applies to an adjustment electrode, according to another embodiment of the inventive concept.
Figure 12:
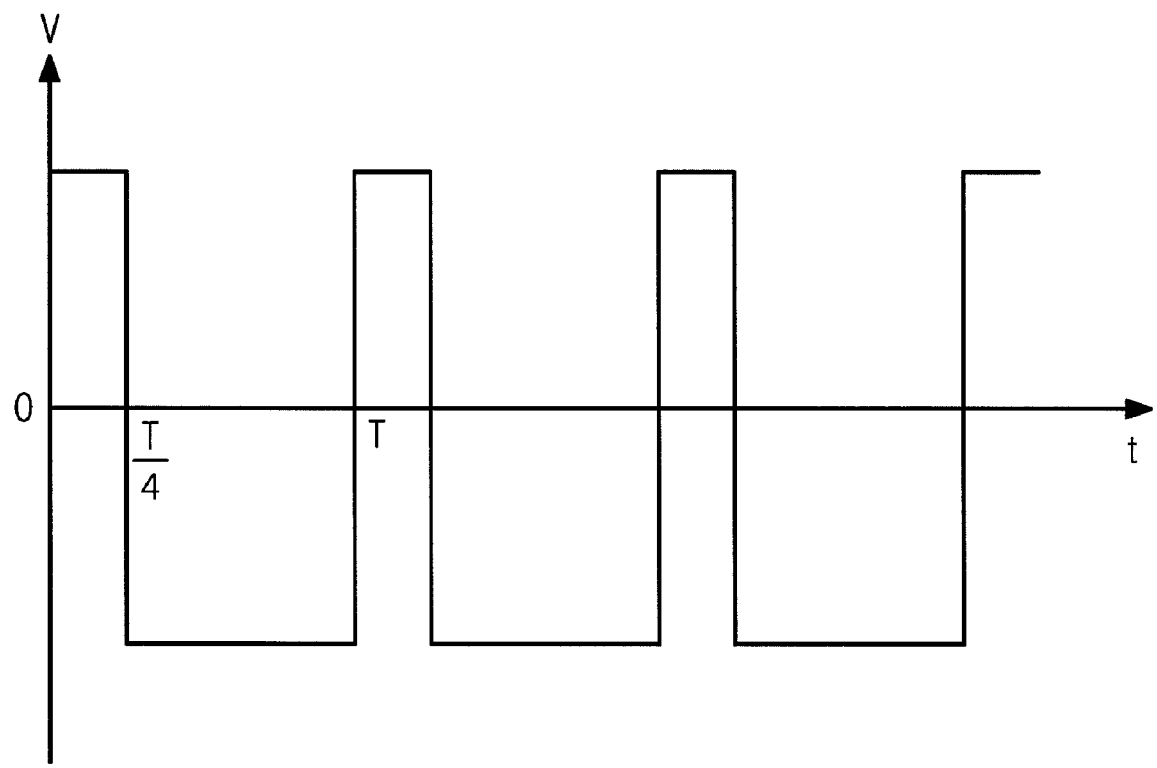
Figure 13:
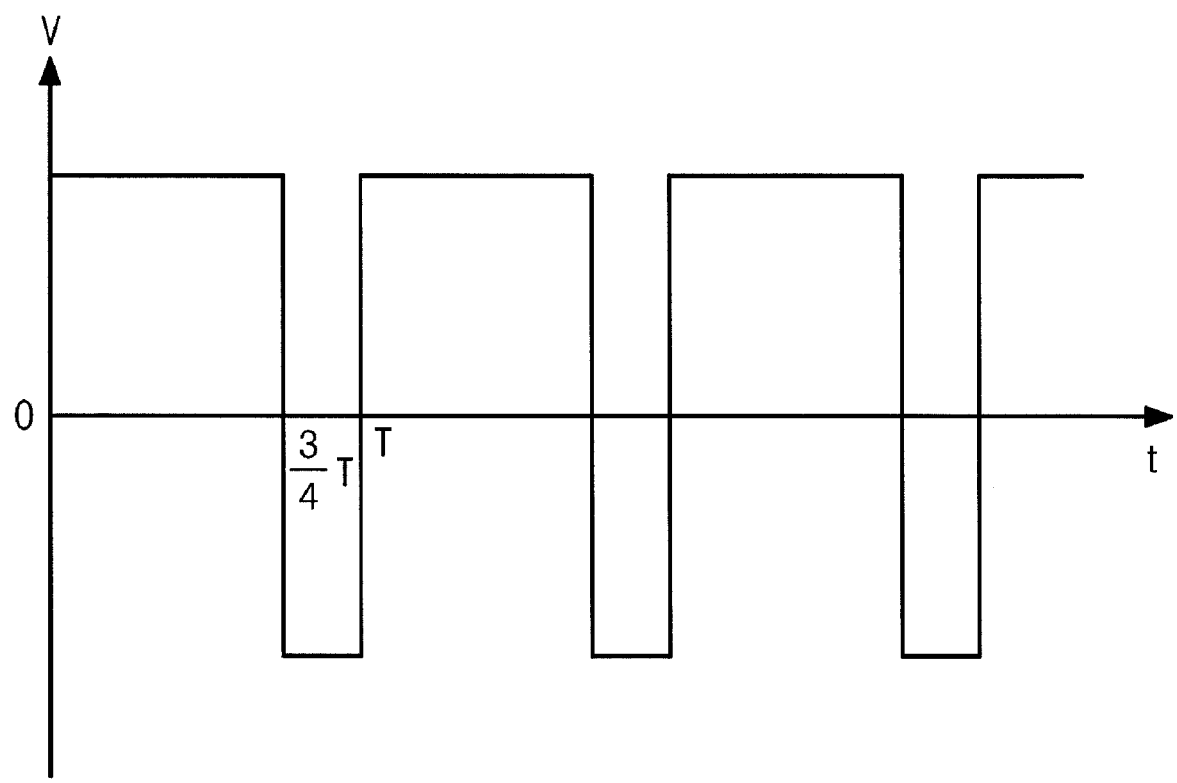

FIGS. 11 to 13 are views illustrating waveforms of electrical signals that an adjustment power supply applies to an adjustment electrode, according to another embodiment of the inventive concept.

According to another embodiment of the inventive concept, the adjustment power supply may apply an electrical signal with a square waveform to the adjustment electrode.

For example, as illustrated in FIG. 11, the adjustment power supply may apply, to the adjustment electrode, a square wave in which positive and negative pulses with predetermined amplitude are alternately repeated.

According to this embodiment, the adjustment power supply does not apply only a signal with the same polarity to one adjustment electrode (e.g., the first adjustment electrode 141 or the second adjustment electrode 142) and may modify the polarity of a signal applied to the adjustment electrode over time. Accordingly, the plasma stimulation apparatus 1 may adjust the distribution of plasma in the cover 11 in time. In other words, according to this embodiment, the plasma stimulation apparatus 1 may adjust not only the spatial distribution but also the temporal distribution of electrons and positive ions in the cover 11.

Furthermore, the adjustment power supply may adjust a square wave such that the time having a positive polarity and the time having a negative polarity are equal to, or different from, each other.

For example, the adjustment power supply may adjust a square wave such that the time having a negative polarity is longer than the time having a positive polarity as illustrated in FIG. 12, or may adjust a square wave such that the time having a positive polarity is longer than the time having a negative polarity as illustrated in FIG. 13.

Figure 14:
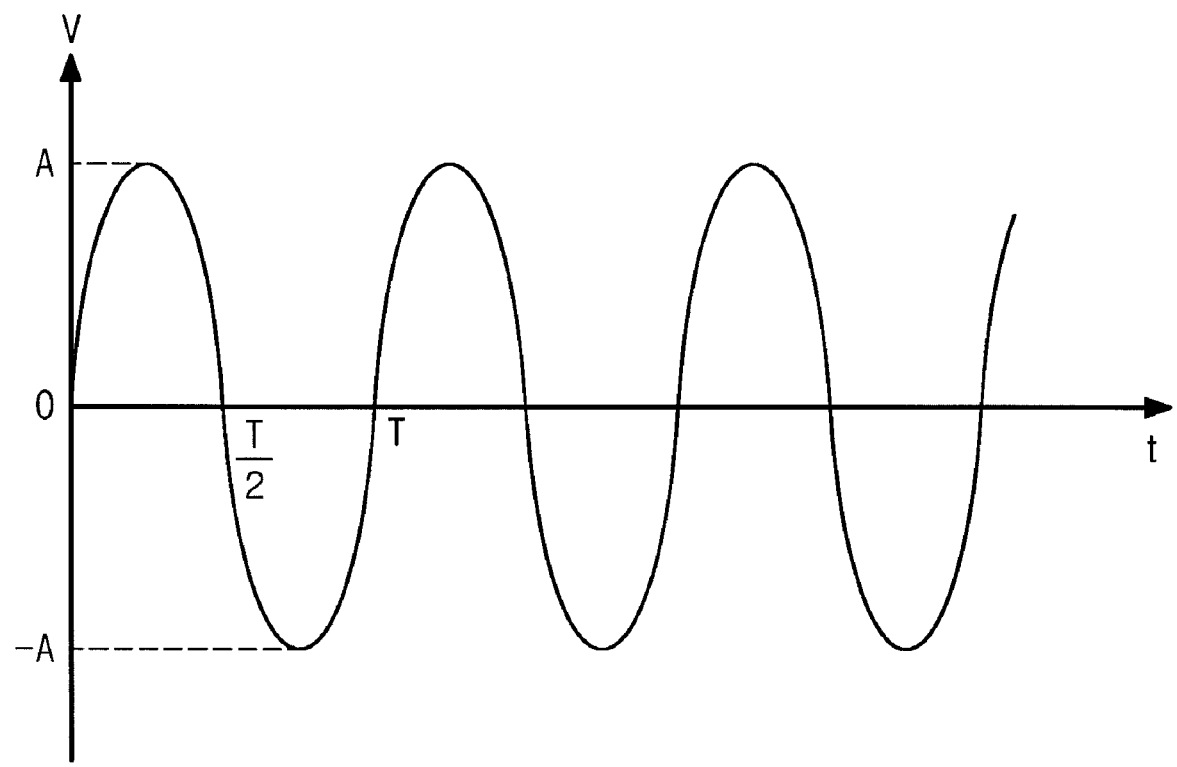
FIGS. 14 to 16 are views illustrating waveforms of electrical signals that an adjustment power supply applies to an adjustment electrode, according to yet another embodiment of the inventive concept.
Figure 15:
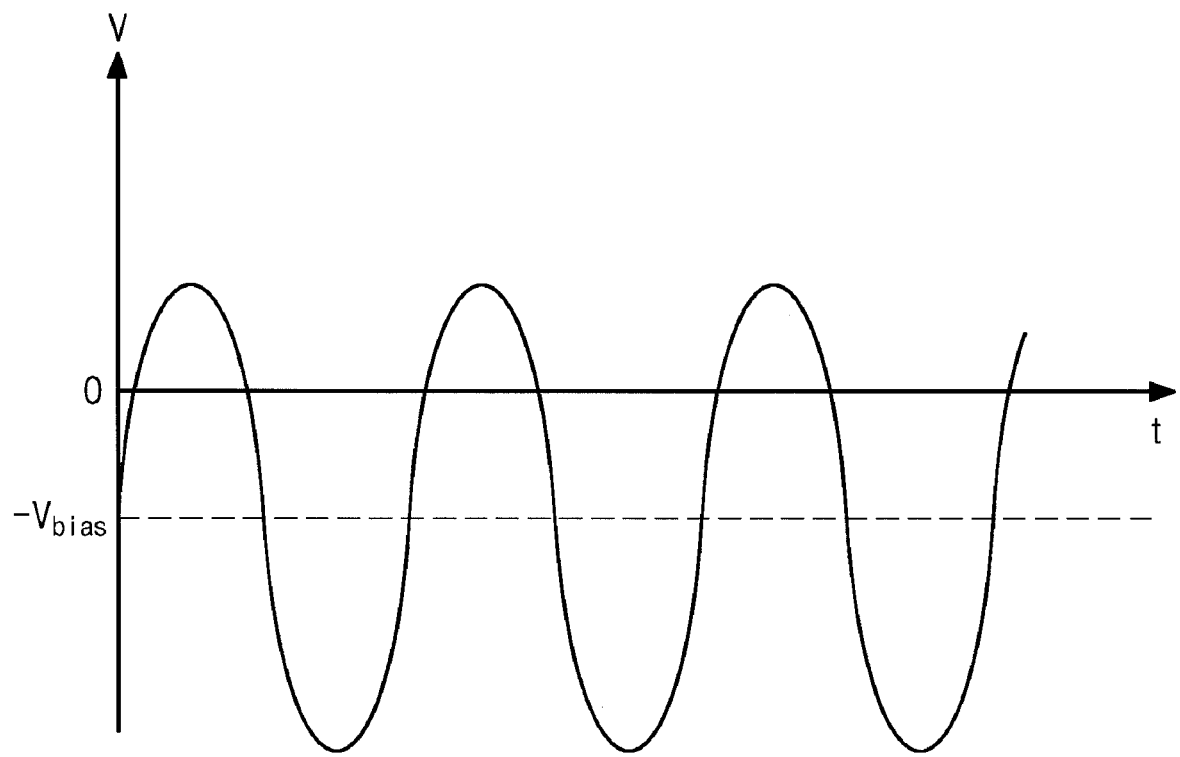
Figure 16:
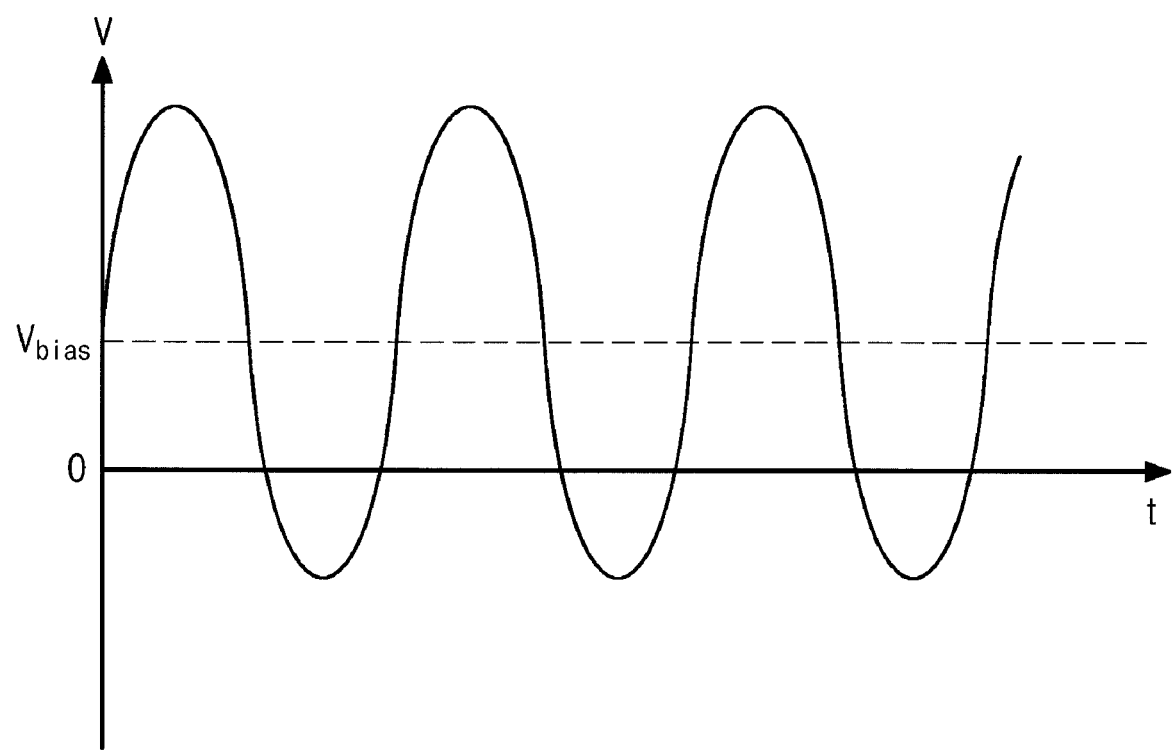

FIGS. 14 to 16 are views illustrating waveforms of electrical signals that an adjustment power supply applies to an adjustment electrode, according to yet another embodiment of the inventive concept.

According to yet another embodiment of the inventive concept, the adjustment power supply may apply an electrical signal with a sinusoidal waveform to the adjustment electrode.

For example, as illustrated in FIG. 14, the adjustment power supply may apply a sinusoidal wave with predetermined amplitude A and frequency 1/T to the adjustment electrode.

According to this embodiment, the plasma stimulation apparatus 1 does not have to separately make a signal with a specific waveform (e.g., the above-described square wave) from an alternating current signal to adjust the distribution of plasma in the cover 11.

In other words, the plasma stimulation apparatus 1 may apply an alternating current signal supplied as power of the apparatus to the adjustment electrode as it is by appropriately adjusting the amplitude A and the frequency 1/T without needing to transform the alternating current signal into a square wave.

As a result, according to this embodiment, the configuration of the adjustment power supply for applying an electrical signal to the adjustment electrode may be simplified, and therefore the complexity of the adjustment power supply may be decreased.

Furthermore, the adjustment power supply may superimpose a direct current signal with a predetermined magnitude on a sinusoidal wave and may apply the superimposed wave to the adjustment electrode.

According to this embodiment, the adjustment power supply may superimpose, on a sinusoidal wave, a direct current signal with a magnitude less than or equal to the amplitude A of the sinusoidal wave and may apply the superimposed wave to the adjustment electrode.

For example, as illustrated in FIG. 15, the adjustment power supply may superimpose, on a sinusoidal wave, a negative direct current signal with a magnitude of $|-V_{bias}|$ less than the amplitude A of the sinusoidal wave and may apply the superimposed wave to the adjustment electrode, or as illustrated in FIG. 16, the adjustment power supply may superimpose, on a sinusoidal wave, a positive direct current signal with a magnitude of $V_{bias}$ less than the amplitude A of the sinusoidal wave and may apply the superimposed wave to the adjustment electrode.

As described above, the adjustment power supply may superimpose a direct current signal on a sinusoidal wave signal to bias the sinusoidal wave in a positive or negative orientation. Accordingly, the adjustment power supply may minimize the complexity of a power circuit and may adjust the time having a positive polarity and the time having a negative polarity in an electrical signal applied to the adjustment electrode.

Figure 17:
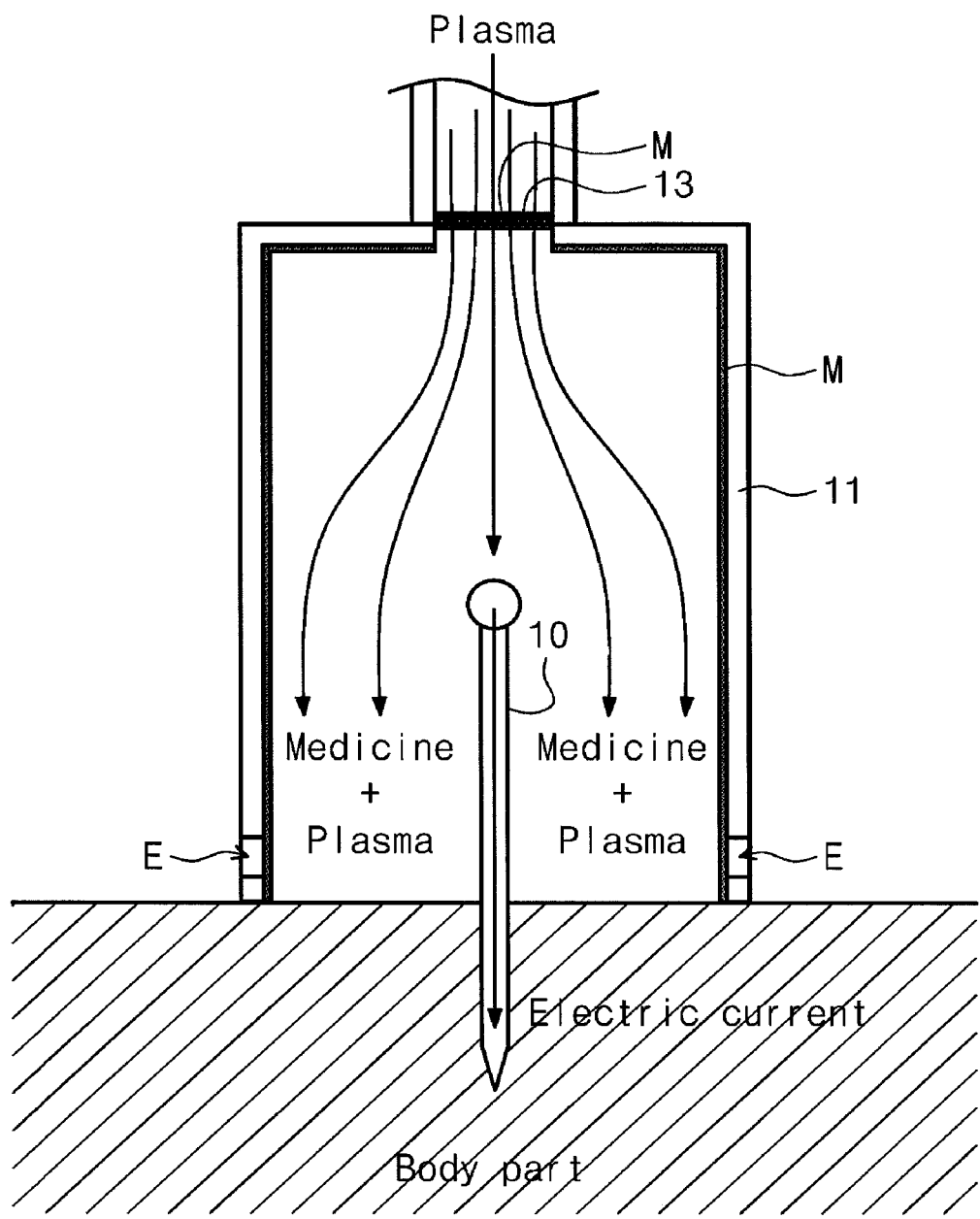
FIG. 17 is a sectional view illustrating a cover according to yet another embodiment of the inventive concept.

FIG. 17 is a sectional view illustrating the cover 11 according to yet another embodiment of the inventive concept.

According to this embodiment, the plasma stimulation apparatus 1 may further include a medicine M applied to at least one of the plasma passage part 13 and an inner surface of the cover 11. The medicine M is intended to enhance treatment effects in stimulation treatment using plasma according to an embodiment of the inventive concept. The medicine M may include various kinds of oriental medicines or western medicines.

Since plasma in this embodiment is generated by the plasma generation unit 12, moves to the cover 11 through the plasma passage part 13, and is provided to a body part along the cover 11, the plasma may be brought into contact with and mixed with the medicine M until reaching the body part after being generated.

In particular, since the plasma passage part 13 is a member through which the plasma necessarily passes while being supplied from the plasma generation unit 12 to the cover 11, the plasma may be sufficiently mixed with the medicine M while passing through the plasma passage part 13.

As a result, as illustrated in FIG. 17, the plasma stimulation apparatus 1 provides the plasma mixed with the medicine M to the body part.

As described above, in this embodiment, the medicine M may be applied to the inside of the cover 11 and the plasma passage part 13 and may be additionally provided to the body part during stimulation treatment. Accordingly, when both the plasma and the medicine M are used for stimulation treatment, improved treatment effects may be obtained, compared with when only the plasma is used for stimulation treatment.

The above-described plasma stimulation apparatus 1 may constitute an acupuncture treatment apparatus together with a needle as the stimulation medium 10 inserted into a body part.

Figure 18:
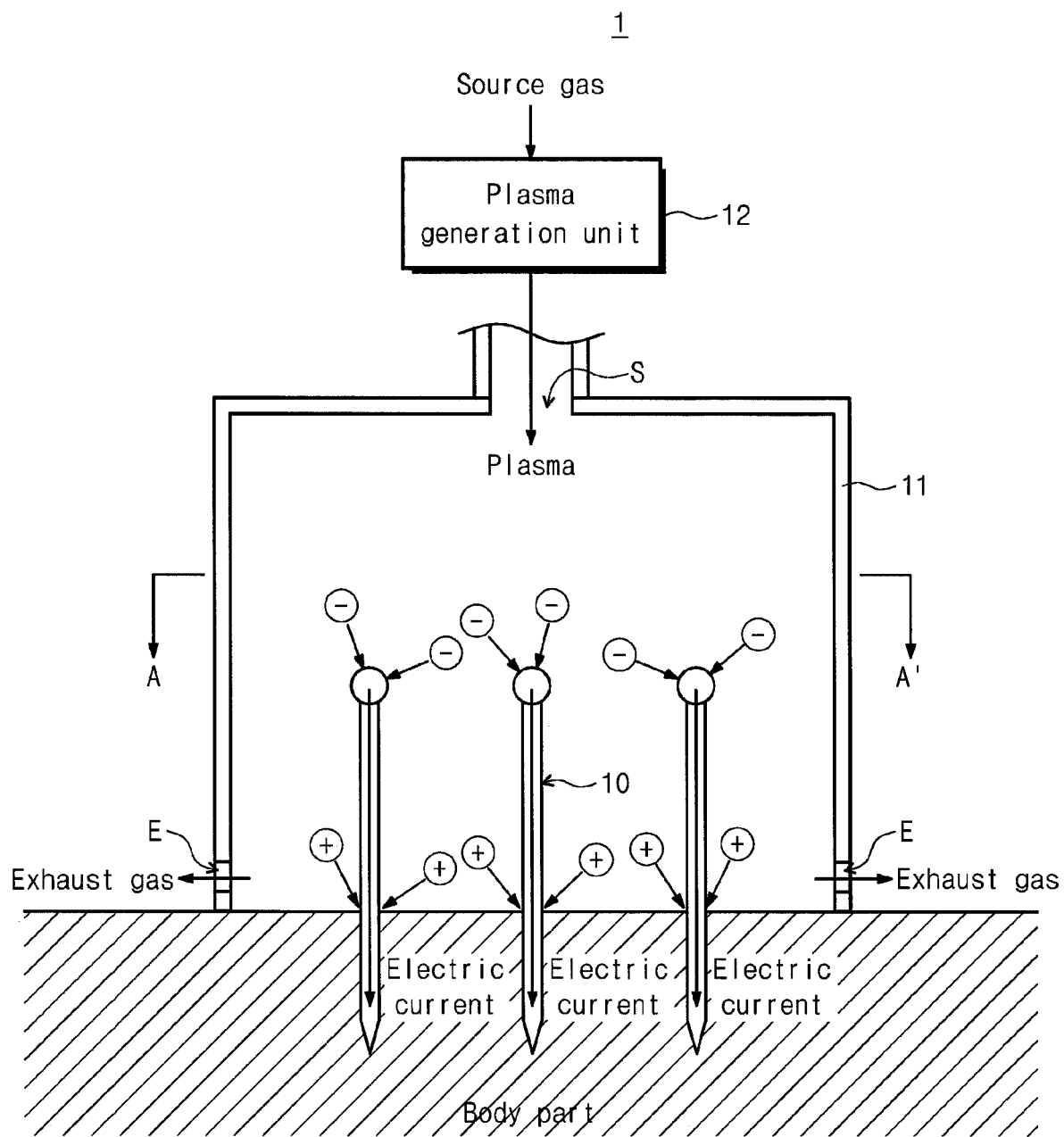
FIG. 18 is a view illustrating an acupuncture treatment apparatus according to an embodiment of the inventive concept.
Figure 19:
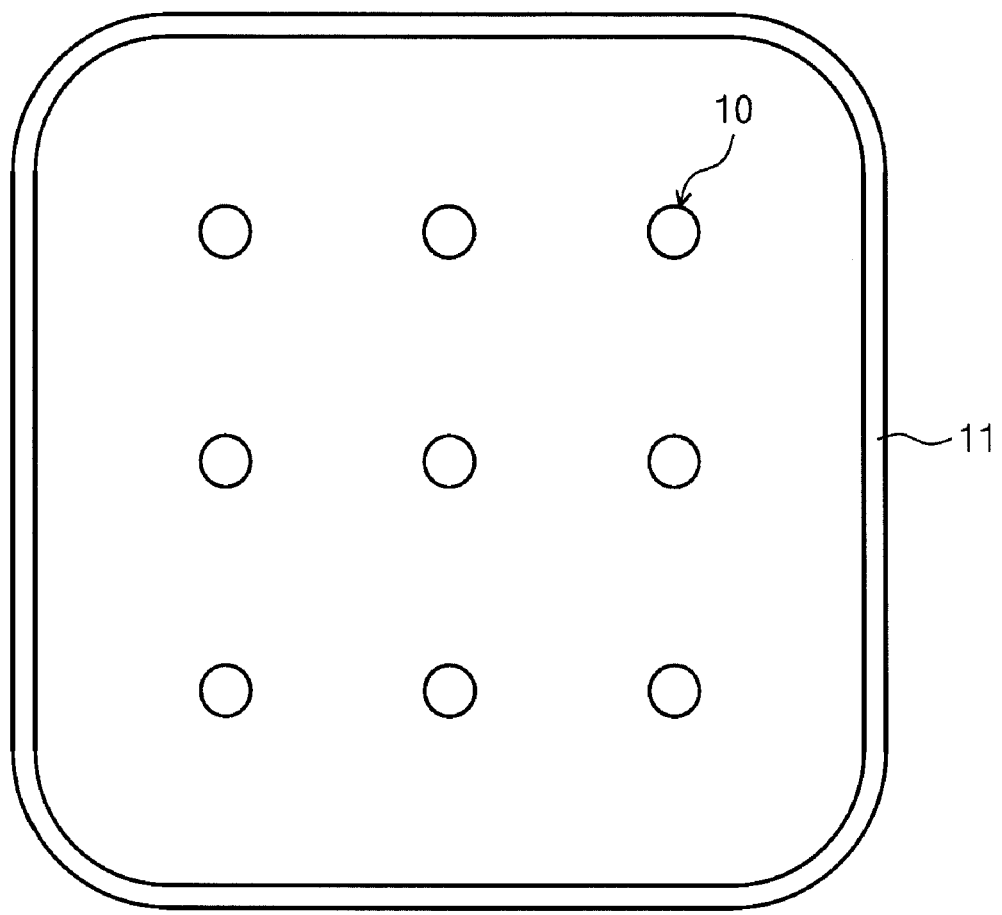
FIG. 19 is a sectional view illustrating the acupuncture treatment apparatus according to an embodiment of the inventive concept.

FIG. 18 is a view illustrating an acupuncture treatment apparatus according to an embodiment of the inventive concept, and FIG. 19 is a sectional view illustrating the acupuncture treatment apparatus according to an embodiment of the inventive concept.

According to an embodiment of the inventive concept, the acupuncture treatment apparatus may include one or more needles 10 inserted into a body part, the cover 11 that covers the needles 10 inserted into the body part, and the plasma generation unit 12 that generates plasma and supplies the plasma to the cover 11.

Unlike in the embodiment of FIG. 1 described above, the plurality of needles 10 are inserted into the body part and the cover 11 has a larger area to cover all of the plurality of the needles 10.

Furthermore, while FIGS. 18 and 19 illustrate an example that the plurality of needles 10 are evenly inserted into the body part, the needles 10 do not necessarily have to be evenly inserted into the body part and may be inserted into a plurality of meridian points that require stimulation.

In addition, at least one of the plasma passage part 13 and the plasma distribution adjustment unit described above may be included even in this embodiment. In particular, in the case where the plurality of needles 10 are inserted into the body part as in this embodiment, the position and area of the second adjustment electrode 142 on the upper surface of the cover 11 may be appropriately determined based on the arrangement of the plurality of needles 10, thereby maximizing electrical stimulation and chemical stimulation through each of the needles 10.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A plasma stimulation apparatus comprising:
   a stimulation medium configured to be inserted into a body part;
   a cover configured to make a contact with the body part in order to form a cover space covering the stimulation medium and the body part;
   a plasma generation unit configured to generate plasma and supply the plasma to the cover space formed by the cover and the body part; and
   a plasma distribution adjustment unit configured to adjust distribution of the plasma in the cover space,
   wherein the plasma distribution adjustment unit comprises:
   a first adjustment electrode formed on a sidewall of the cover that surrounds the simulation medium;
   a second adjustment electrode formed on an upper wall of the cover that faces the body part; and
   an adjustment power supply configured to apply an electrical signal to the first and second adjustment electrodes.

2. The plasma stimulation apparatus of claim 1, wherein the cover is made of a dielectric material.

3. The plasma stimulation apparatus of claim 1, wherein the cover includes a supply hole through which the cover receives the plasma from the plasma generation unit.

4. The plasma stimulation apparatus of claim 3, further comprising:
   a plasma passage part located between the plasma generation unit and the supply hole and configured to pass the plasma, with the plasma passage part in a grounded state.

5. The plasma stimulation apparatus of claim 4, wherein the plasma passage part includes a mesh configured to block an area through which the plasma passes.

6. The plasma stimulation apparatus of claim 1, wherein the cover includes an exhaust hole configured to discharge an exhaust gas, the exhaust hole being located adjacent to a contact surface of the cover that makes contact with the body part.

7. The plasma stimulation apparatus of claim 1, wherein the plasma generation unit includes:
   a dielectric material having an empty space through which a source gas for generating the plasma passes;
   a first electrode located inside the dielectric material; and
   a second electrode configured to surround at least part of the dielectric material.

8. The plasma stimulation apparatus of claim 7, wherein the plasma generation unit receives an inert gas as the source gas.

9. The plasma stimulation apparatus of claim 1, wherein the adjustment power supply applies a direct current signal to the first and second adjustment electrodes.

10. The plasma stimulation apparatus of claim 9, wherein the adjustment power supply applies a direct current signal with a negative polarity to the first adjustment electrode and a direct current signal with a positive polarity to the second adjustment electrode.

11. The plasma stimulation apparatus of claim 4, further comprising:
- a medicine applied to at least one of the plasma passage part and an inner surface of the cover.

12. An acupuncture treatment apparatus comprising:
- at least one needle configured to be inserted into a body part;
- a cover configured to make a contact with the body part in order to form a cover space covering the at least one needle and the body part;
- a plasma generation unit configured to generate plasma and supply the plasma to the cover space formed by the cover and the body part; and
- a plasma distribution adjustment unit configured to adjust distribution of the plasma in the cover space,
- wherein the plasma distribution adjustment unit comprises:
  - a first adjustment electrode formed on a sidewall of the cover that surrounds the simulation medium;
  - a second adjustment electrode formed on an upper wall of the cover that faces the body part; and
  - an adjustment power supply configured to apply an electrical signal to the first and second adjustment electrodes.

* * * * *